United States Patent [19]

Loper et al.

[11] Patent Number: 5,377,693
[45] Date of Patent: Jan. 3, 1995

[54] THIGH AND LEG ALIGNMENT APPARATUS

[76] Inventors: Edward C. Loper; Christine B. Berger, both of 7125 Castor Ave., Philadelphia, Pa. 19149

[21] Appl. No.: 177,770

[22] Filed: Jan. 4, 1994

[51] Int. Cl.⁶ .............................................. A61F 5/00
[52] U.S. Cl. ...................................... 128/845; 2/227; 602/24; 128/891
[58] Field of Search .................... 602/23, 24; 128/845, 128/846, 882, 891, 892; 2/227, 214; 482/105

[56] References Cited

U.S. PATENT DOCUMENTS

| | | | |
|---|---|---|---|
| D. 311,791 | 10/1990 | Koldofsky et al. | |
| 1,592,496 | 7/1926 | Madden | 602/61 X |
| 3,508,550 | 4/1970 | Vollrath | 128/891 X |
| 3,559,211 | 2/1971 | Malisani, Jr. | |
| 4,384,369 | 5/1983 | Prince | 482/105 X |
| 4,876,745 | 10/1989 | Richards | |
| 4,914,753 | 4/1990 | Chang | |
| 5,077,837 | 1/1992 | Meistrell | |
| 5,105,473 | 4/1992 | Valtakari | 2/227 X |
| 5,123,407 | 6/1992 | Dewhurst | 602/62 X |
| 5,269,323 | 12/1993 | Krouskop | 128/845 |

*Primary Examiner*—Richard J. Apley
*Assistant Examiner*—Linda C. Dvorak

[57] ABSTRACT

A new and improved thigh and leg alignment apparatus includes a pants assembly which includes a first inner thigh portion adapted to be located above a wearer's knee when the pants assembly is worn. A first leg portion is adapted to be located below a wearer's knee when the pants assembly is worn. Also, the pants assembly includes a second inner thigh portion adapted to be located above a wearer's knee when the pants assembly is worn; and a second leg portion is adapted to be located below a wearer's knee when the pants assembly is worn. The first inner thigh portion is opposed to the second inner thigh portion, and the first leg portion is opposed to the second leg portion. A first inner thigh pocket is connected to the first inner thigh portion of the pants assembly, and a first inner thigh cushion is placed in the first inner thigh pocket. A second inner thigh pocket is connected to the second inner thigh portion of the pants assembly, and a second inner thigh cushion is placed in the second inner thigh pocket. A first inner leg pocket is connected to the first leg portion of the pants assembly, and a first inner leg cushion placed in the first inner leg pocket. A second inner leg pocket is connected to the second leg portion of the pants assembly, and a second inner leg cushion is placed in the second inner leg pocket.

2 Claims, 2 Drawing Sheets

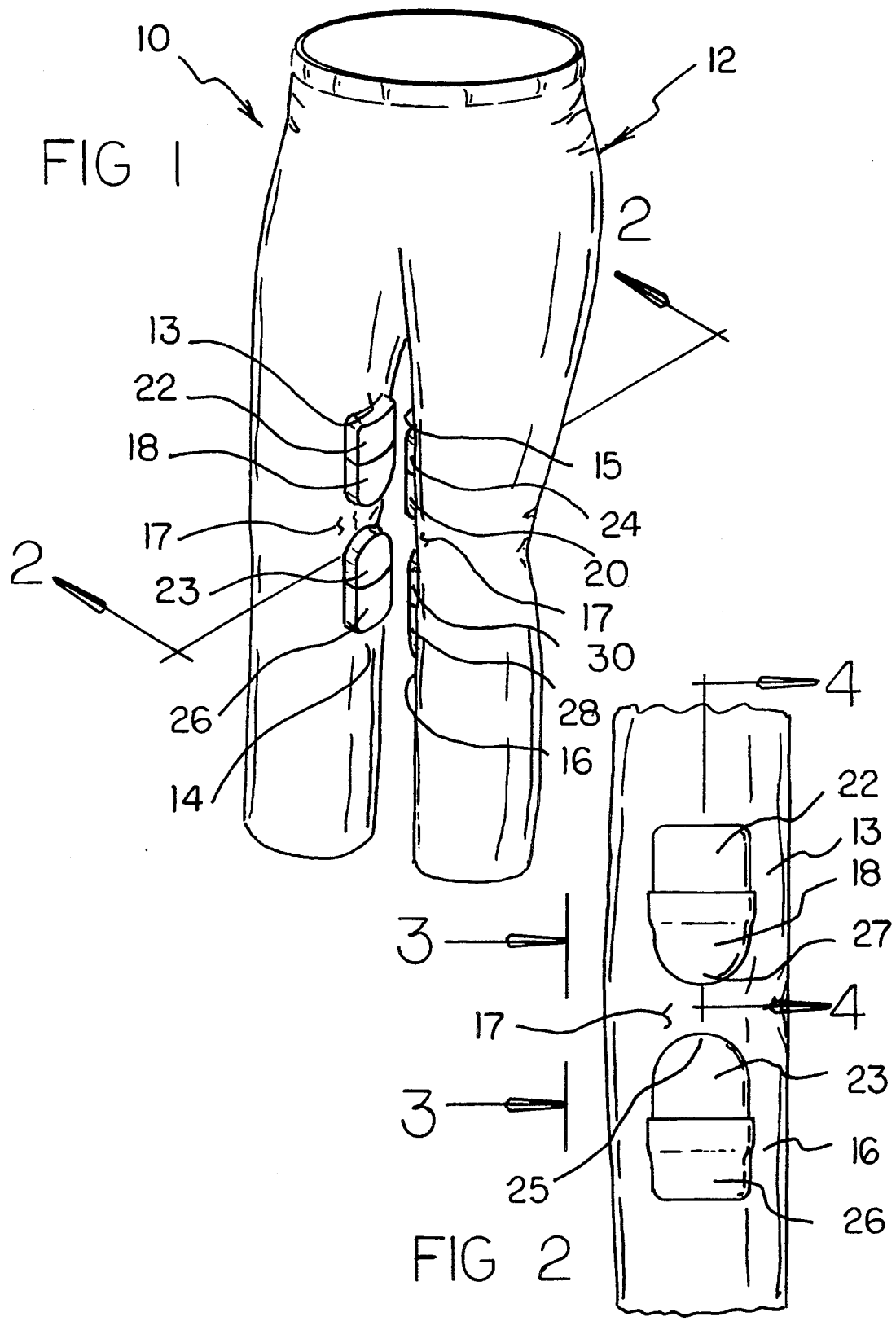

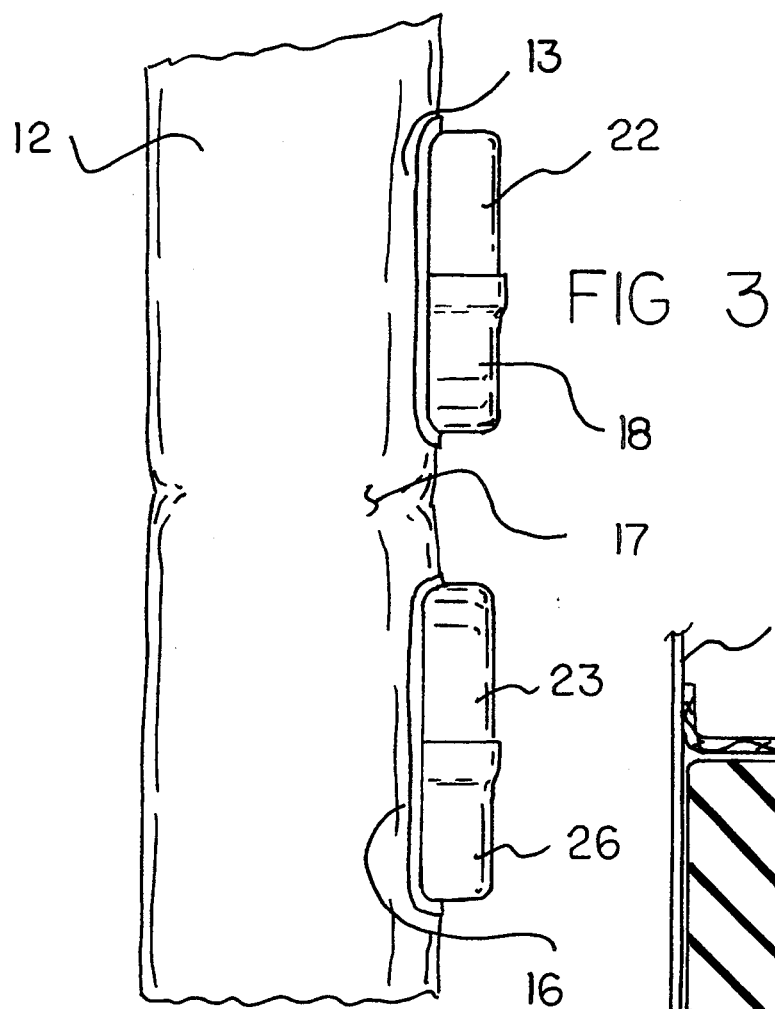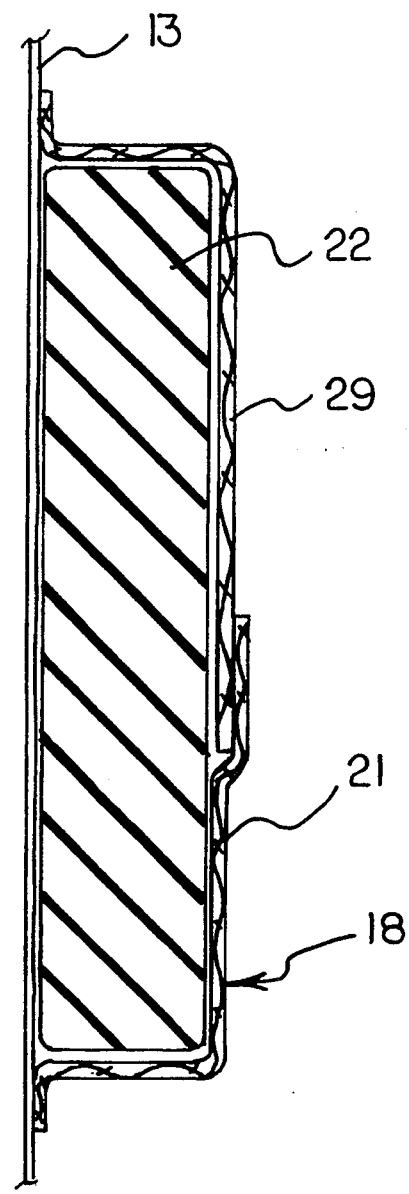

THIGH AND LEG ALIGNMENT APPARATUS

BACKGROUND OF THE INVENTION

1. Field of the Invention

The present invention relates generally to devices for aiding proper alignment of body parts, and, more particularly, to devices especially adapted for properly aligning a person's legs.

2. Description of the Prior Art

Backaches are a pervasive health problem that affects millions of people at one time or another. The causes of backaches are varied, but one cause that affects many people is a misalignment of the spine. Misalignment of the spine may be exacerbated during a person's sleeping hours when various sleeping positions may contribute to spine misalignment. In this respect, it would be desirable if a device were provided that assists in the alignment of the spine when a person is sleeping.

Doctors, chiropractors, and other medical personnel often recommend that a person sleep with a conventional pillow between their legs to assist in spine alignment. The pillow serves as a thick shim to provide a space between the legs. In addition, to keep the pillow between the legs, the legs must be maintained, in a proper alignment. Although a person may begin a night's sleep with a pillow between one's legs, during the night, as a result of tossing and turning, the pillow is often displaced from its position between the legs. In this respect, it would be desirable if a device were provided which furnishes a thick shim to provide a space between a person's legs without being displaced by a person's tossing; and turning during a night's sleep.

A person's lower appendage includes a thigh, a knee, a leg and a foot. Of greatest importance in assisting in keeping a spine in proper alignment are the thigh and the leg. Of course the knee bends between the thigh and the leg. In this respect, it would be desirable if a device were provided that keeps opposite thighs properly spaced apart, that keeps opposite legs properly spaced apart, and that permits opposite knees to bend.

People vary considerably in their body dimensions. In this respect, it would be desirable if a thigh and leg alignment apparatus were provided that is adaptable to people of different sizes and dimensions.

Many people, when they go to sleep, wear sleepwear, such as pajamas. If a thigh and leg alignment apparatus is employed, it would be desirable if the thigh and leg alignment apparatus could be incorporated into sleepwear. If this were done, then employing the thigh and leg alignment apparatus would not be a strange and foreign task. In this respect, it would be desirable if a thigh and leg alignment apparatus were provided that is incorporated in sleepwear such as pajamas.

When placed between a person's thighs and legs, a conventional pillow provides a soft cushion between the thighs and legs. Pillows vary quite a bit in their composition. Some include feathers; some include artificial foam. Some pillows are inflatable and include air as the cushioning substance. In this respect, it would be desirable if a thigh and leg alignment apparatus can include a variety of cushioning materials.

During a night's sleep, people often get up and get out of bed for a number of reasons and then return to bed. In this respect, it would be desirable if a thigh and leg alignment device were provided which is readily reemployed after a person returns to bed during the night.

During a night's sleep, as a person tosses and turns, a thigh and leg alignment apparatus may be moved out of alignment. Even so, the device should not have sharp edges and be uncomfortable so as to cause the wearer to be awakened from slumber. In this respect, it would be desirable if a thigh and leg alignment device were provided which has a low profile and soft edges so as not to cause a wearer's discomfort if the device is placed out of alignment.

With a thigh and leg alignment apparatus in the form of sleepwear, it is important that the sleepwear be readily launderable. In this respect, the cushions may be readily removed from the sleepwear, and the sleepwear may be laundered without the cushions. Afterwards, the cushions can be placed back in the sleepwear. Optionally, the cushions also may be launderable.

Pajamas may be made from a wide variety of fabrics, and many persons may have preferences of one fabric over another. A person may even have a favorite pair of pajamas that one would not like to give up using in order to employ a thigh and leg alignment apparatus. In this respect, it would be desirable if conventional pajamas could be retrofitted to become a thigh and leg alignment apparatus.

It may be of interest that, throughout the years, a number of innovations have been developed relating to protecting knees from trauma, and the following U.S. patents are representative of some of those innovations: U.S. Pat. No. 3,559,211; 4,876,745; 4,914,753; 5,077,837; and U.S. Pat. Des. Nos. 311,791. None of the devices disclosed in these cited patents are disclosed as being suitable for thigh and leg alignment of opposite thighs and legs as a person sleeps.

Thus, while the foregoing body of prior art indicates it to be well known to use a conventional pillow to align a person's thighs and legs, the prior art described above does not teach or suggest a thigh and leg alignment apparatus which has the following combination of desirable features: (1) assists in the alignment of the spine when a person is sleeping; (2) furnishes a thick shim to provide a space between a person's thighs and legs without being displaced by a person's tossing and turning during a night's sleep; (3) keeps opposite thighs properly spaced apart, keeps opposite legs properly spaced apart, and permits opposite knees to bend; (4) is adaptable to people of different sizes and dimensions; (5) is incorporated in sleepwear such as pajamas; (6) can include a variety of cushioning materials; (7) is readily reemployed after a person gets out of bed and returns to bed during the night; (8) has a low profile and soft edges so as not to cause a wearer's discomfort if the device is placed out of alignment; (9) employs cushions that may be readily removed from the sleepwear so that the sleepwear may be laundered without the cushions; and (10) permits conventional pajamas to be retrofitted to become a thigh and leg alignment apparatus. The foregoing desired characteristics are provided by the unique thigh and leg alignment apparatus of the present invention as will be made apparent from the following description thereof. Other advantages of the present invention over the prior art also will be rendered evident.

SUMMARY OF THE INVENTION

To achieve the foregoing and other advantages, the present invention, briefly described, provides a new and improved thigh and leg alignment apparatus which includes a pants assembly which includes a first inner thigh portion adapted to be located above a wearer's knee when the pants assembly is worn. The pants assembly includes a first leg portion adapted to be located below a wearer's knee when the pants assembly is worn. Also, the pants assembly includes a second inner thigh portion adapted to be located above a wearer's knee when the pants assembly is worn; and the pants assembly includes a second leg portion adapted to be located below a wearer's knee when the pants assembly is worn. The first inner thigh portion is opposed to the second inner thigh portion, and the first leg portion is opposed to the second leg portion. A first inner thigh pocket is connected to the first inner thigh portion of the pants assembly, and a first inner thigh cushion is placed in the first inner thigh pocket. A second inner thigh pocket is connected to the second inner thigh portion of the pants assembly, and a second inner thigh cushion is placed in the second inner thigh pocket.

A first inner leg pocket is connected to the first leg portion of the pants assembly, and a first inner leg cushion placed in the first inner leg pocket. A second inner leg pocket is connected to the second leg portion of the pants assembly, and a second inner leg cushion is placed in the second inner leg pocket.

Each of the first inner thigh cushion, the second inner thigh cushion, the first inner leg cushion, and the second inner leg cushion may include a rounded end. The first inner thigh cushion and the second inner thigh cushion are oriented so that the respective rounded ends face downward toward the knee region. The first inner leg cushion and the second inner leg cushion are oriented so that the respective rounded ends face upward toward the knee region. The first inner thigh pocket and the second inner thigh pocket may include a rounded end for receiving respective rounded ends of respective inner thigh cushions.

A conventional pajama pants can be retrofitted in accordance with the principles of the invention. More specifically, a first inner thigh pocket can be sewn onto the pajama pants on a first inner thigh portion of the pajama pants. Similarly, a second inner thigh pocket can be sewn onto the pajama pants on a second inner thigh portion of the pajama pants. A first inner thigh cushion is placed in the first inner thigh pocket, and a second inner thigh cushion is placed in the second inner thigh pocket. In this way, the pajama pants are retrofitted in accordance with the thigh and leg alignment apparatus of the invention.

In addition, a first inner leg pocket can be sewn onto the pajama pants a first leg portion. A second inner leg pocket can be sewn onto the pajama pants at a second leg portion. A first inner leg cushion can be placed in the first inner leg pocket, and a second inner leg cushion can be placed in the second inner leg pocket. In this additional way, the pajama pants are retrofitted in accordance with the thigh and leg alignment apparatus of the invention.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining a preferred embodiment of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

Further, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

It is therefore an object of the present invention to provide a new and improved thigh and leg alignment apparatus which has all of the advantages of the prior art and none of the disadvantages.

It is another object of the present invention to provide a new and improved thigh and leg alignment apparatus which may be easily and efficiently manufactured and marketed.

It is a further object of the present invention to provide a new and improved thigh and leg alignment apparatus which is of durable and reliable construction.

An even further object of the present invention is to provide a new and improved thigh and leg alignment apparatus which is susceptible of a low cost of manufacture with regard to both materials and labor, and which accordingly is then susceptible of low prices of sale to the consuming public, thereby making such thigh and leg alignment apparatus available to the buying public.

Still yet a further object of the present invention is to provide; a new and improved thigh and leg alignment apparatus which assists in the alignment of the spine when a person is sleeping.

Still another object of the present invention is to provide a new and improved thigh and leg alignment apparatus that furnishes a thick shim to provide a space between a person's thighs and legs without being displaced by a person's tossing and turning during a night's sleep.

Yet another object of the present invention is to provide a new and improved thigh and leg alignment apparatus which keeps opposite thighs properly spaced apart, keeps opposite legs properly spaced apart, and permits opposite knees to bend.

Even another object of the present invention is to provide a new and improved thigh and leg alignment apparatus that is adaptable to people of different sizes and dimensions.

Still a further object of the present invention is to provide a new and improved thigh and leg alignment apparatus which is incorporated in sleepwear such as pajamas.

Yet another object of the present invention is to provide a new and improved thigh and leg alignment apparatus that can include a variety of cushioning materials.

Still another object of the present invention is to provide a new and improved thigh and leg alignment apparatus which is readily reemployed after a person get out of bed and returns to bed during the night.

Yet another object of the present invention is to provide a new and improved thigh and leg alignment apparatus that has a low profile and soft edges so as not to cause a wearer's discomfort if the device is placed out of alignment.

Still a further object of the present invention is to provide a new and improved thigh and leg alignment apparatus that employs cushions that may be readily removed from the sleepwear so that the sleepwear may be laundered without the cushions.

An even further object of the present invention is to provide a new and improved thigh and leg alignment apparatus which permits conventional pajamas to be retrofitted to become a thigh and leg alignment apparatus.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein:

FIG. 1 is a perspective view showing a preferred embodiment of the thigh and leg alignment apparatus of the invention.

FIG. 2 is an enlarged partial top view of a portion of the embodiment of the invention shown in FIG. 1 taken along line 2—2 of FIG. 1.

FIG. 3 is an enlarged side view of the portion of the embodiment of the invention shown in FIG. 2 taken along line 3—3 thereof.

FIG. 4 is an enlarged cross-sectional view of a pocket portion of the embodiment of the invention shown in FIG. 2 taken along line 4—4 of FIG. 2.

DESCRIPTION OF THE PREFERRED EMBODIMENT

With reference to the drawings, a new and improved thigh and leg alignment apparatus embodying the principles and concepts of the present invention will be described.

Turning to FIGS. 1-4, there is shown an exemplary embodiment of the thigh and leg alignment apparatus of the invention generally designated by reference numeral 10. In its preferred form, thigh and leg alignment apparatus 10 includes a pants assembly 12 which includes a first inner thigh portion 13 adapted to be located above a wearer's knee shown as general region 17 when the pants assembly 12 is worn. The pants assembly 12 includes a first leg portion 14 adapted to be located below a wearer's knee when the pants assembly 12 is worn. Also, the pants assembly 12 includes a second inner thigh portion 15 adapted to be located above a wearer's knee when the pants assembly 12 is worn; and the pants assembly 12 includes a second leg portion 16 adapted to be located below a wearer's knee when the pants assembly 12 is worn. The first inner thigh portion 13 is opposed to the second inner thigh portion 15, and the first leg portion 14 is opposed to the second leg portion 16. A first inner thigh pocket 18 is connected to the first inner thigh portion 13 of the pants assembly 12, and a first inner thigh cushion 22 is placed in the first inner thigh pocket 18. As shown in FIG. 4, the first inner thigh pocket 18 can include a bottom portion 21 and an upper flap portion 29. A second inner thigh pocket 20 is connected to the second inner thigh portion 15 of the pants assembly 12, and a second inner thigh cushion 24 is placed in the second inner thigh pocket 20.

A first inner leg pocket 26 is connected to the first leg portion 14 of the pants assembly 12, and a first inner leg cushion 23 placed in the first inner leg pocket 26. A second inner leg pocket 28 is connected to the second leg portion 16 of the pants assembly 12, and a second inner leg cushion 30 is placed in the second inner leg pocket 28.

Each of the first inner thigh cushion 22, the second inner thigh cushion 24, the first inner leg cushion 23, and the second inner leg cushion 30 includes a rounded end 25. The first inner thigh cushion 22 and the second inner thigh cushion 24 are oriented so that the respective rounded ends 25 face downward toward the knee region 17. The first inner leg cushion 23 and the second inner leg cushion 30 are oriented so that the respective rounded ends 25 face upward toward the knee region 17. The first inner thigh pocket 18 and the second inner thigh pocket 20 includes a rounded end 27 for receiving respective rounded ends 25 of respective inner thigh cushions.

In use, a person pulls on the pants assembly 12. With the first inner thigh cushion 22 in the first inner thigh pocket 18, with the second inner thigh cushion 24 in the second inner thigh pocket 20, with the first inner leg cushion 23 in the first inner leg pocket 26, and with the second inner leg cushion 30 in the second inner leg pocket 28, when the person lies down in bed and when the person places the second inner thigh cushion 24 on the first inner thigh cushion 22 and the second inner leg cushion 30 on the first inner leg cushion 23, the person's legs, thighs, and spine are placed in desired alignment.

Since the respective thigh pockets and cushions are located above the person's knees which underlie region 17, and since the respective leg pockets and cushions are located below the person's knees, the person is readily able to flex one's knees with the thigh and leg alignment apparatus 10 of the invention is worn.

In a modified version of the thigh and leg alignment apparatus of the invention, the respective leg pockets and leg cushions need not be present. In this version only the respective thigh pockets and thigh cushions may be used with the pants assembly 12 of the invention.

A conventional pajama pants can be retrofitted in accordance with the principles of the invention. More specifically, a first inner thigh pocket 18 can be sewn onto the pajama pants on a first inner thigh portion 13 of the pajamas pants. Similarly, a second inner thigh pocket 20 can be sewn onto the pajama pants on a second inner thigh portion 15 of the pajama pants. A first inner thigh cushion 22 is placed in the first inner thigh pocket 18, and a second inner thigh cushion 24 is placed in the second inner thigh pocket 20. In this way, the pajama pants are retrofitted in accordance with the thigh and leg alignment apparatus of the invention.

In addition, a first inner leg pocket 26 can be sewn onto the pajama pants at a first leg portion 14. A second inner leg pocket 28 can be sewn onto the pajama pants at a second leg portion 16. A first inner leg cushion 23 can be placed in the first inner leg pocket 26, and a second inner leg cushion 30 can be placed in the second inner leg pocket 28. In this additional way, the pajama pants are retrofitted in accordance with the thigh and leg alignment apparatus of the invention.

The components of the thigh and leg alignment apparatus of the invention can be made from inexpensive and durable cloth and plastic materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved thigh and leg alignment apparatus that is low in cost, relatively simple in design and operation, and which may advantageously be used to assist in the alignment of the spine when a person is sleeping. With the invention, a thigh and leg alignment apparatus is provided which furnishes a thick shim to provide a space between a person's thighs and legs without being displaced by a person's tossing and turning during a night's sleep. With the invention, a thigh and leg alignment apparatus is provided which keeps opposite thighs properly spaced apart, keeps opposite legs properly spaced apart, and permits opposite knees to bend. With the invention, a thigh and leg alignment apparatus is provided which is adaptable to people of different sizes and dimensions. With the invention, a thigh and leg alignment apparatus is provided which is incorporated in sleepwear such as pajamas. With the invention, a thigh and leg alignment apparatus is provided which can include a variety of cushioning materials. With the invention, a thigh and leg alignment apparatus is provided which is readily reemployed after a person get out of bed and returns to bed during the night. With the invention, a thigh and leg alignment apparatus is provided which has a low profile and soft edges so as not to cause a wearer's discomfort if the device is placed out of alignment. With the invention, a thigh and leg alignment apparatus is provided which employs cushions that may readily removed from the sleepwear so that the sleepwear may be laundered without the cushions. With the invention, a thigh and leg alignment apparatus is provided which permits conventional pajamas to be retrofitted to become a thigh and leg alignment apparatus.

With respect to the above description, it should be realized that the optimum dimensional relationships for the parts of the invention, to include variations in size, form function and manner of operation, assembly and use, are deemed readily apparent and obvious to those skilled in the art, and therefore, all relationships equivalent to those illustrated in the drawings and described in the specification are intended to be encompassed only by the scope of appended claims.

While the present invention has been shown in the drawings and fully described above with particularity and detail in connection with what is presently deemed to be the most practical and preferred embodiments of the invention, it will be apparent to those of ordinary skill in the art that many modifications thereof may be made without departing from the principles and concepts set forth herein. Hence, the proper scope of the present invention should be determined only by the broadest interpretation of the appended claims so as to encompass all such modifications and equivalents.

What is claimed as being new and desired to be protected by Letters Patent of the United States is as follows:

1. A new and improved thigh and leg alignment apparatus, comprising:

a pants assembly which includes a first inner thigh portion adapted to be located above a wearer's knee when said pants assembly is worn, said pants assembly including a first leg portion adapted to be located below a wearer's knee when said pants assembly is worn, said pants assembly including a second inner thigh portion adapted to be located above a wearer's knee when said pants assembly is worn, said pants assembly including a second leg portion adapted to be located below a wearer's knee when said pants assembly is worn, said first inner thigh portion being opposed to said second inner thigh portion, and said first leg portion being opposed to said second leg portion, a first inner thigh pocket connected to said first inner thigh portion of said pants assembly, a first inner thigh cushion placed in said first inner thigh pocket, a second inner thigh pocket connected to said second inner thigh portion of said pants assembly, a second inner thigh cushion placed in said second inner thigh pocket, a first inner leg pocket connected to said first leg portion of said pants assembly, a first inner leg cushion placed in said first inner leg pocket, a second inner leg pocket connected to said second leg portion of said pants assembly, a second inner leg cushion placed in said second inner leg pocket, wherein said first inner thigh cushion, said second inner thigh cushion, said first inner leg cushion, and said second inner leg cushion include a rounded end, wherein said first inner thigh cushion and said second inner thigh cushion are oriented so that said respective rounded ends face downward toward the knee region, and wherein said first inner leg cushion and said second inner leg cushion are oriented so that said respective rounded ends face upward toward the knee region.

2. The apparatus described in claim 1 wherein said first inner thigh pocket and said second inner thigh pocket include a rounded end for receiving respective rounded ends of respective inner thigh cushions.

* * * * *